United States Patent
Potter et al.

(10) Patent No.: US 10,939,964 B2
(45) Date of Patent: Mar. 9, 2021

(54) SYSTEM FOR DETECTING CATHETER ELECTRODES ENTERING INTO AND EXITING FROM AN INTRODUCER

(71) Applicant: St. Jude Medical, Atrial Fibrillation Division, Inc., St. Paul, MN (US)

(72) Inventors: Daniel J. Potter, Stillwater, MN (US); Lev A. Koyrakh, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 953 days.

(21) Appl. No.: 15/609,534

(22) Filed: May 31, 2017

(65) Prior Publication Data

US 2017/0325899 A1 Nov. 16, 2017

Related U.S. Application Data

(63) Continuation of application No. 13/839,963, filed on Mar. 15, 2013, now Pat. No. 9,693,820.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 5/063* (2013.01); *A61B 5/065* (2013.01);
(Continued)

(58) Field of Classification Search
None
See application file for complete search history.

(56) References Cited

U.S. PATENT DOCUMENTS

| 7,263,397 B2 | 8/2007 | Hauck et al. |
| 7,386,339 B2 | 6/2008 | Strommer et al. |

(Continued)

FOREIGN PATENT DOCUMENTS

| CN | 102036606 A | 4/2011 |
| EP | 2 462 869 B1 | 6/2012 |

(Continued)

OTHER PUBLICATIONS

Kabra et al., "Recent Trends in Imaging for Atrial Fibrillation Ablation", Indian Pacing and Electrophysiology Journal, May 5, 2010, pp. 215-227, XP055048854.
(Continued)

*Primary Examiner* — Jonathan Cwern
(74) *Attorney, Agent, or Firm* — Dykema Gossett PLLC

(57) ABSTRACT

Systems for detecting when catheter electrodes enter into and exit from an introducer are disclosed. In one form, a system detects a relative position of a catheter (comprising a marker band and an electrode) and an introducer (comprising a proximity sensor adapted to sense the marker band), while the catheter and introducer are in a human body. The system may comprise an electronic control unit to analyze signals from the catheter and/or the introducer, to determine whether the catheter electrode is within the introducer; and to disregard data collected from the electrode when that electrode is in the introducer. The sensor may be on the catheter and the sensed element may be on the introducer. The sensed element may comprise one or several marker bands. A marker band may be applied during the manufacture of a medical device or during its use and is any element capable of electromagnetic detection.

16 Claims, 13 Drawing Sheets

(51) Int. Cl.
*A61M 25/01* (2006.01)
*A61B 18/14* (2006.01)
*A61B 17/00* (2006.01)
*A61B 18/00* (2006.01)
*A61M 25/00* (2006.01)
*A61B 90/00* (2016.01)

(52) U.S. Cl.
CPC ..... *A61B 18/1492* (2013.01); *A61M 25/0105* (2013.01); *A61B 5/066* (2013.01); *A61B 2017/00243* (2013.01); *A61B 2018/00023* (2013.01); *A61B 2018/00351* (2013.01); *A61B 2018/00577* (2013.01); *A61B 2018/00892* (2013.01); *A61B 2018/00988* (2013.01); *A61B 2034/2051* (2016.02); *A61B 2034/2053* (2016.02); *A61B 2090/061* (2016.02); *A61B 2090/0811* (2016.02); *A61B 2562/0257* (2013.01); *A61M 25/0097* (2013.01); *A61M 25/0147* (2013.01); *A61M 2025/0166* (2013.01)

(56) References Cited

U.S. PATENT DOCUMENTS

| | | | |
|---|---|---|---|
| 7,720,521 B2 * | 5/2010 | Chang | A61B 17/24 600/424 |
| 8,560,042 B2 | 10/2013 | Markowitz et al. | |
| 2002/0032380 A1 | 3/2002 | Acker et al. | |
| 2006/0098921 A1 | 5/2006 | Benaron et al. | |
| 2007/0185397 A1 * | 8/2007 | Govari | A61B 5/042 600/424 |
| 2008/0140006 A1 | 6/2008 | Eskuri et al. | |
| 2008/0146942 A1 | 6/2008 | Dala-Krishna | |
| 2008/0255470 A1 | 10/2008 | Hauck et al. | |
| 2009/0262109 A1 | 10/2009 | Markowitz et al. | |
| 2009/0265128 A1 * | 10/2009 | Markowitz | A61B 34/20 702/94 |
| 2010/0036238 A1 * | 2/2010 | Neidert | A61B 34/20 600/424 |
| 2011/0230758 A1 | 9/2011 | Eichler | |
| 2011/0295240 A1 | 12/2011 | Hamel et al. | |
| 2012/0089038 A1 | 4/2012 | Ryu et al. | |
| 2012/0130230 A1 | 5/2012 | Eichler et al. | |
| 2012/0173217 A1 | 7/2012 | Heimbecher | |
| 2013/0303886 A1 | 11/2013 | Ludwin et al. | |
| 2014/0275991 A1 | 9/2014 | Potter et al. | |

FOREIGN PATENT DOCUMENTS

| | | |
|---|---|---|
| JP | 2006-255440 A | 9/2006 |
| WO | 2007/014063 A2 | 2/2007 |
| WO | 2008/082802 A2 | 7/2008 |
| WO | 2009/129475 A1 | 10/2009 |
| WO | 2009/152486 A1 | 12/2009 |
| WO | 2010/075292 A1 | 7/2010 |
| WO | 2012/173697 A1 | 12/2012 |

OTHER PUBLICATIONS

International Search Report for PCT Application No. 2014/018706, dated Jun. 2, 2014, 3 pages.

* cited by examiner

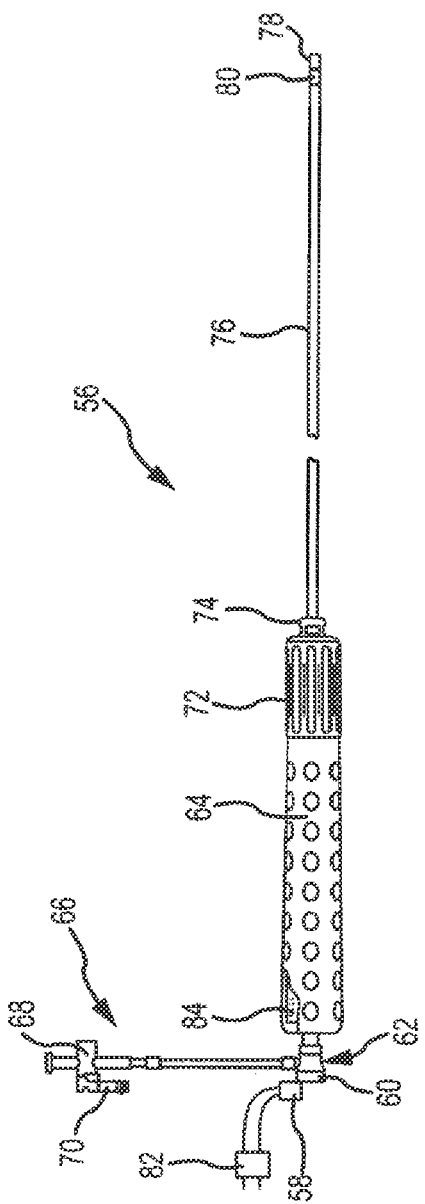
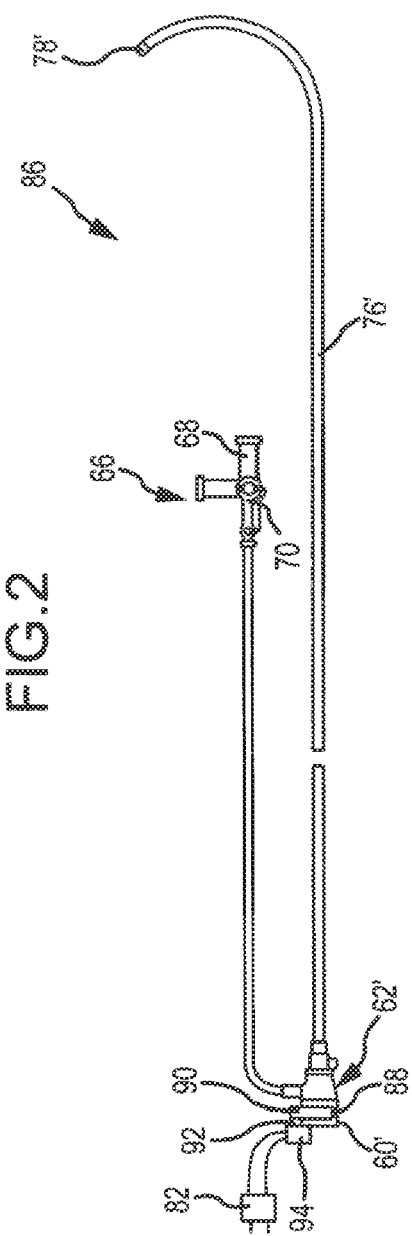
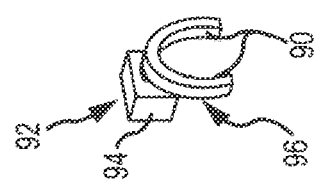

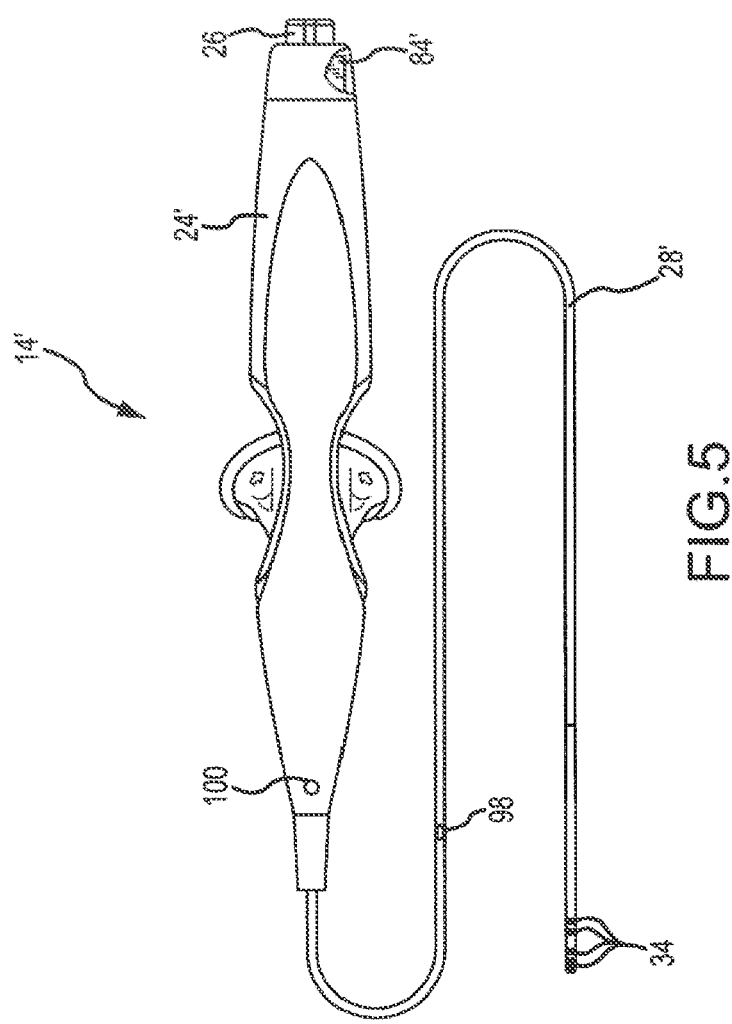

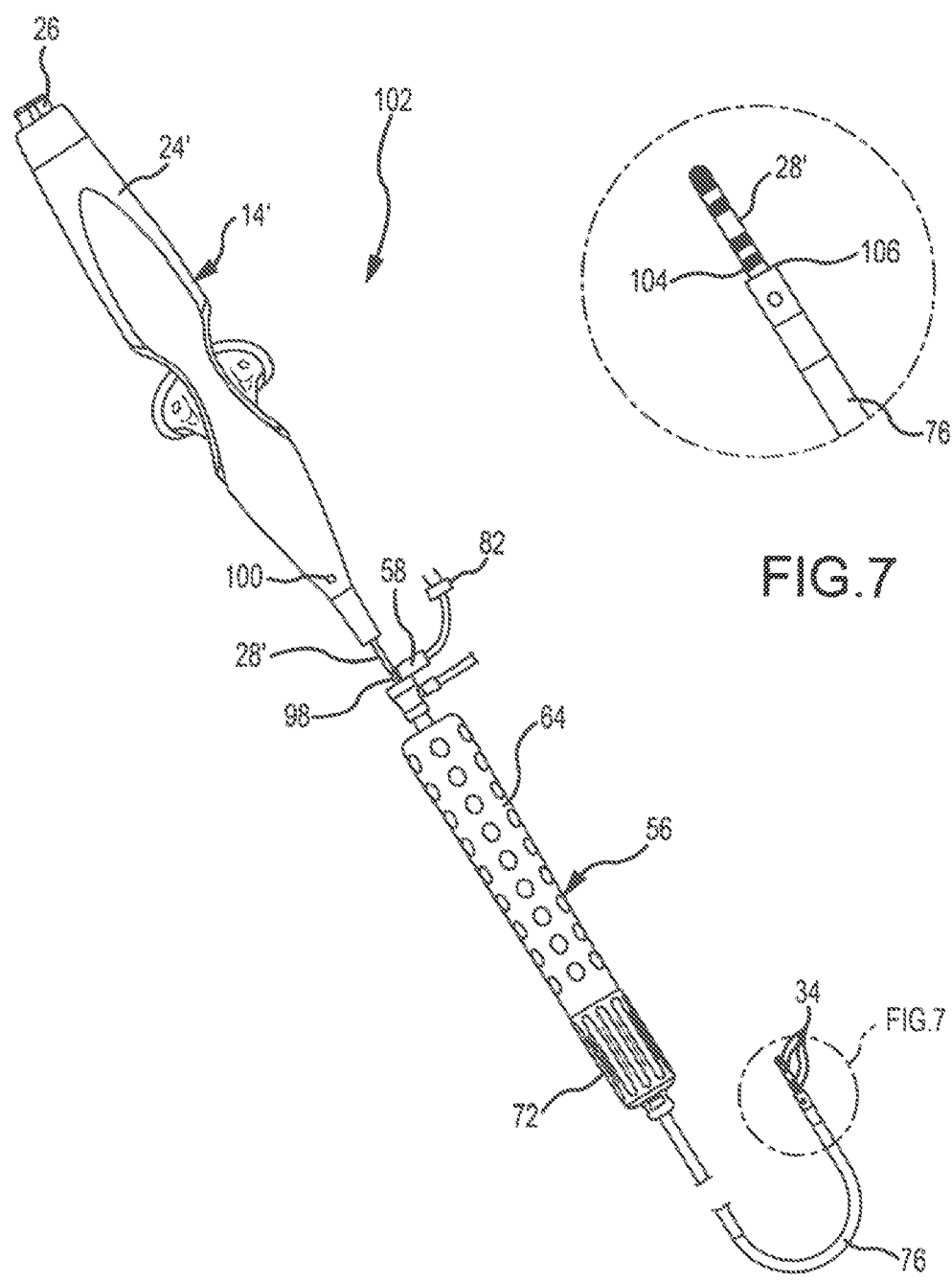

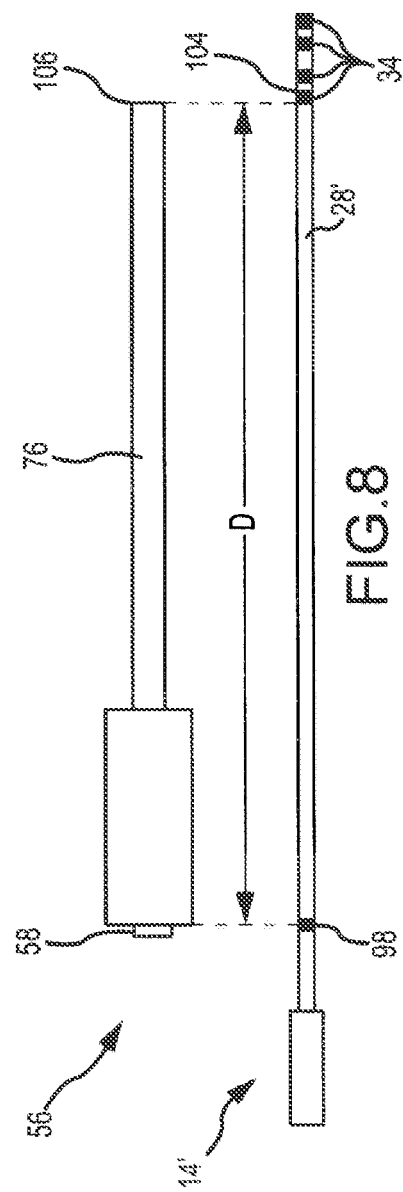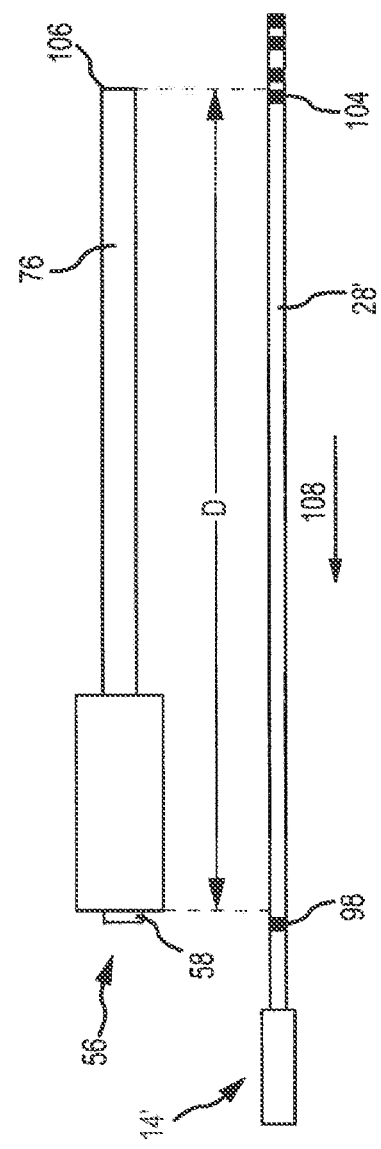

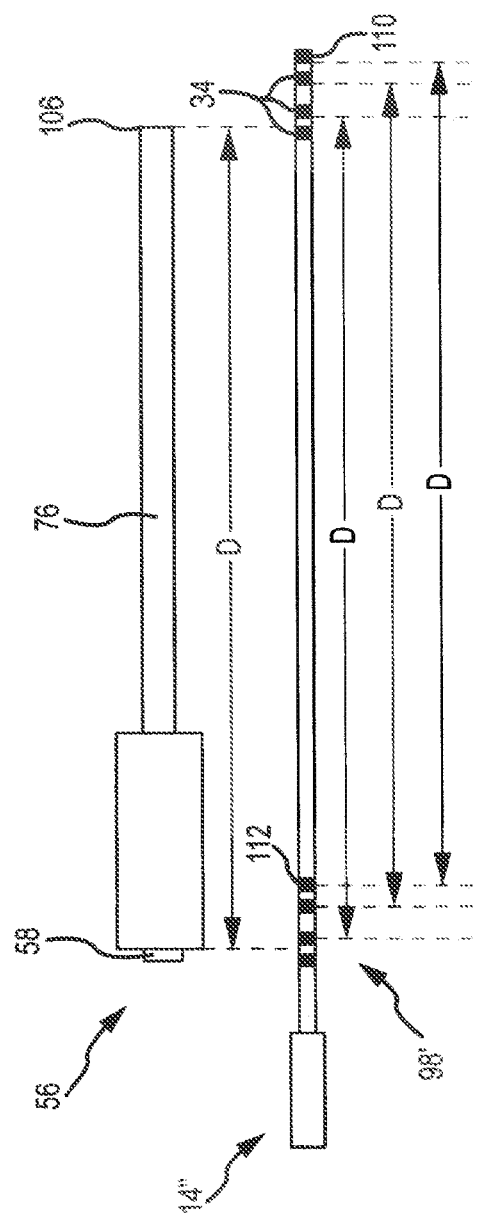

SYSTEM FOR DETECTING CATHETER ELECTRODES ENTERING INTO AND EXITING FROM AN INTRODUCER

CROSS-REFERENCE TO RELATED APPLICATIONS

This application is a continuation of U.S. application Ser. No. 13/839,963, filed 15 Mar. 2013, now U.S. Pat. No. 9,693,820, which is hereby incorporated by reference as though fully set forth herein.

BACKGROUND OF THE INVENTION a. Field of the Invention

This invention relates to systems, apparatuses and methods for navigating a medical device within a body. In particular, the instant invention relates to systems, apparatuses and methods for detecting when one or more electrodes on a medical device enter into and/or exit from an introducer or other enveloping device while navigating the medical device within a body.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. This lesion disrupts undesirable cardiac activation pathways and thereby limits, corrals, or prevents errant conduction signals that can form the basis for arrhythmias.

To position a catheter at a desired site within the body, some type of navigation may be used, such as using mechanical steering features incorporated into the catheter (or an introducer). In some examples, medical personnel may manually manipulate and/or operate the catheter using the mechanical steering features.

In order to facilitate the advancement of catheters through a patient's vasculature, a navigating system may be used. Such navigating systems may include, for example, electric-field-based positioning and navigating systems that are able to determine the position and orientation of the catheter (and similar devices) within the body. In such electric-field-based positioning and navigating systems, it can be important to know when the electrodes on the catheter are shielded inside of a sheath or introducer that is being used to deliver the catheter to a desired location.

The foregoing discussion is intended only to illustrate the present field and should not be taken as a disavowal of claim scope.

BRIEF SUMMARY OF THE INVENTION

The present disclosure generally relates to detecting when catheter electrodes enter into, and/or exit from, an introducer or other enveloping device in order to avoid, for example, introducing undesirable shift or drift into the determined catheter position and orientation based upon readings obtained by an electric-field-based positioning system.

In an embodiment, a system detects a relative position of a catheter and an introducer while the catheter and the introducer are in a human body, wherein the catheter comprises a marker band and an electrode and the introducer comprises a proximity sensor adapted to sense the marker band. The system comprising (a) an electric-field-based positioning system; and (b) an electronic control unit electrically coupled to the electric-field-based positioning system. The electronic control unit is operable to do the following: (A) drive currents through a plurality of patch electrodes on a surface of the body and measure a resulting voltage from the catheter electrode; (B) monitor a first signal originating from the proximity sensor to determine when the marker band pass the proximity sensor; (C) analyze the first signal to determine whether the catheter electrode is within the introducer; and (D) disregard the measured resulting voltage if the catheter electrode is within the introducer. In some embodiments, when the system disregards measured resulting voltage data, it also communicates that fact to a clinician (e.g., by sending a message to a display or activating a light on the catheter or the introducer).

In another embodiment, a system detects when a sensed element on a first medical device enter into or exist from an introducer, and the system comprises the following: (a) a first storage operable to store (i) first location data relating to a location of the sensed element on the first medical device and (ii) second location data relating to a location of a sensor on the introducer; (b) a second storage operable to store current position and orientation data relating to the first medical device; (c) a device operable to determine a relative position of the sensor and the sensed element based upon the stored first and second location data; and (d) a processor in communication with the first storage, the second storage, and the device. Further, in this embodiment, the processor is operable to do the following: (1) consider the relative position of the sensor and the sensed element; (2) determine whether to disregard the current position and orientation data for the first medical device; and (3) output a signal indicative of whether the current position and orientation data for the first medical device is being disregarded.

In yet another embodiment, a system detects when one or more catheter electrodes enter into or exist from an introducer, and the system comprises the following: (a) an introducer comprising (i) an introducer proximal end, (ii) an introducer distal end, (iii) a longitudinally-extending introducer body extending between the introducer proximal end and the introducer distal end; and (iv) a first element affixed to the introducer body; and (b) a catheter comprising (i) a catheter proximal end, (ii) a catheter distal end, (iii) a longitudinally-extending catheter body extending between the catheter proximal end and the catheter distal end; (iv) a plurality of electrodes on the catheter body; and (v) a second element affixed to the catheter body and operable to electromagnetically interact with the first element. In one offshoot of this embodiment, the first element is a proximity sensor and the second element is a marker band on an outer surface of the catheter body. And, in another embodiment, the catheter comprising part of the system may further comprise an indicator light configured to report when at least one of the plurality of catheter electrodes is located within the introducer.

In another embodiment, a catheter is provided that includes a shaft having one or more electrodes at a distal portion of the shaft, and includes a detectable marker positioned proximal to the one or more electrodes at the distal portion of the shaft. The detectable marker is positioned at a predetermined distance from a most proximal one of the one or more electrodes. In a more particular embodiment of such a catheter, the predetermined distance may correspond to a distance from a distal opening of an interoperable introducer to a marker detector positioned along the introducer proximal to the distal opening. In still another particular embodiment of such a catheter, one or more additional detectable markers may each be positioned proximal to a plurality of the electrodes at the distal portion of the shaft, where each of the detectable markers is positioned a predetermined distance from a respective one of the plurality the electrodes.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2 depicts a steerable introducer having a sensor affixed to its proximal end.

FIG. 3 depicts a fixed-curve introducer having a sensor detachably connected to its proximal end.

FIG. 4 is an isometric view of a detachable sensor.

FIG. 5 depicts an ablation catheter having a marker band on its shaft and on-board information storage in its handle.

FIG. 6 depicts a catheter assembly comprising the catheter of FIG. 5 inserted through the steerable introducer of FIG. 2.

FIG. 7 is an enlarged view of the circled region of FIG. 6, depicting a most-proximal catheter electrode adjacent to the distal end of the introducer shaft.

FIGS. 8 and 9 schematically depict the catheter and introducer depicted in, for example, FIGS. 2, 5, and 6, and demonstrate how a change in the location of the marker band relative to the sensor corresponds to a change in the position of the most-proximal catheter electrode relative to the distal end of the introducer.

FIG. 11 is similar to FIGS. 8 and 9, but schematically depicts the introducer and catheter shown in FIG. 10, wherein the catheter comprises a separate marker band for each electrode.

DETAILED DESCRIPTION OF THE INVENTION

Figure 1:
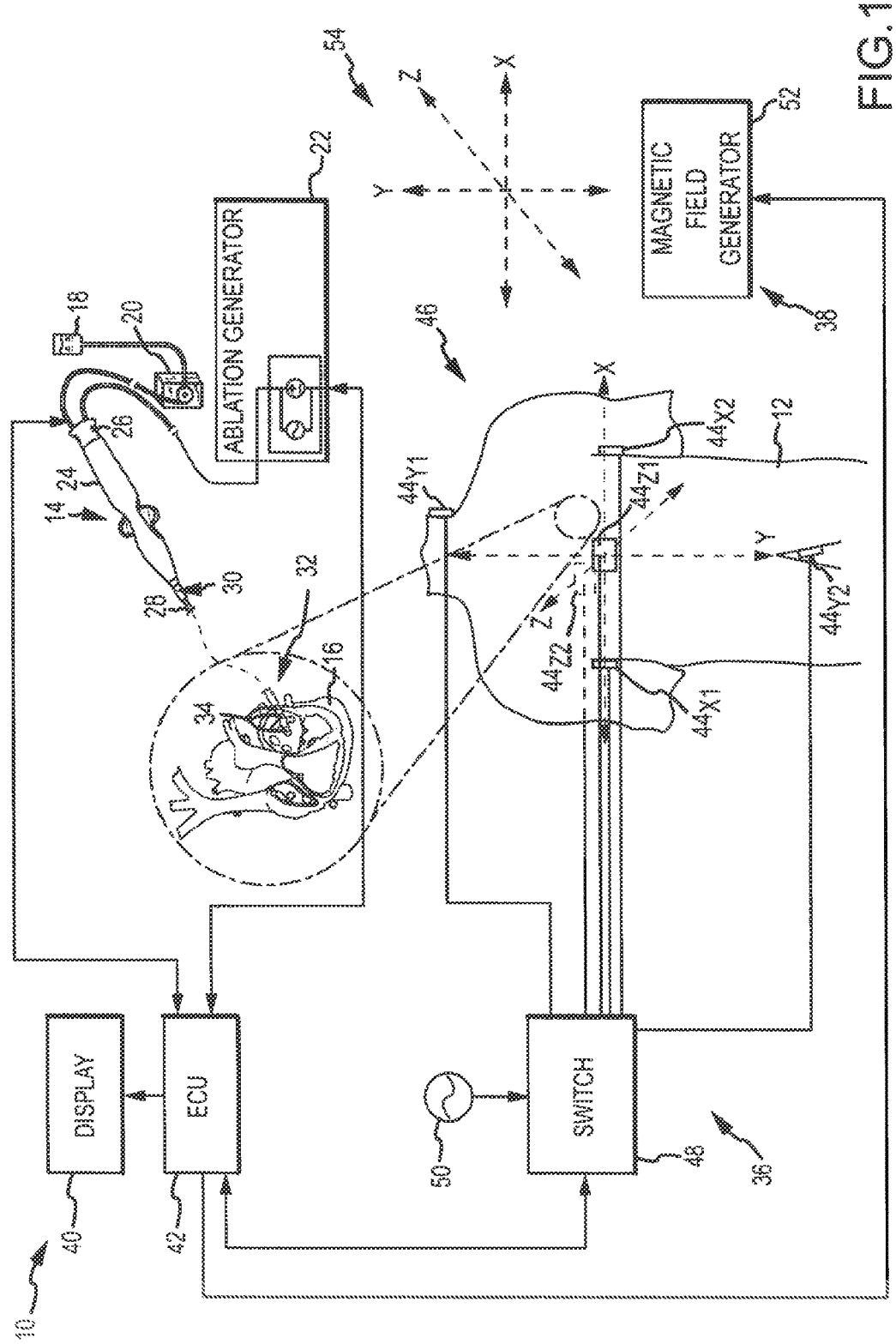
FIG. 1 is diagrammatic view of one embodiment of a system for navigating a medical device within a body.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart that has been exploded away from the body 12. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate an electrophysiological mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, fluids, or surgical tools. The shaft 28 may be introduced into a blood vessel or other structure within the body 12 through a conventional introducer (see, for example, FIGS. 2 and 3). The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments.

The system 10 may include an electric-field-based positioning system 36, a magnetic-field-based positioning system 38, a display 40, and an electronic control unit (ECU) 42. Each of the exemplary system components is described further below.

The electric-field-based positioning system 36 is provided to determine the position and orientation of the catheter 14 and similar devices within the body 12. The system 36 may comprise, for example, the ENSITE NAVX system sold by St. Jude Medical, Inc. of St. Paul, Minn., and described in, for example, U.S. Pat. No. 7,263,397 titled "Method and Apparatus for Catheter Navigation and Location. Mapping in the Heart," the entire disclosure of which is hereby incorporated by reference as though fully set forth herein. The system 36 operates based upon the principle that when low amplitude electrical signals are passed through the thorax, the body 12 acts as a voltage divider (or potentiometer or rheostat) such that the electrical potential or field strength measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch 44X1, left side patch 44X2, neck patch 44Y1, leg patch 44Y2, chest patch 44Z1, and back patch 44Z2; and each patch electrode is connected to a switch 48 (e.g., a multiplex switch) and a signal generator 50. The patch electrodes 44X1, 44X2 are placed along a first (x) axis; the patch electrodes 44Y1, 44Y2 are placed along a second (y) axis, and the patch electrodes 44Z1, 44Z2 are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are proportional to the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and the switch 48 of the electric-field-based positioning system 36, and magnetic generator 52 of the magnetic-field-based positioning system 38. For example, the ECU 42 may be configured through appropriate software to provide control signals to switch 48 and thereby sequentially couple pairs of patch electrodes 44 to the signal generator 50. Excitation of each pair of electrodes 44 generates an electromagnetic field within the body 12 and within an area of interest such as the heart. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40. The depicted ECU 42 represents any processing arrangement such as, for example, single device processors, multiple device processors (e.g., co-processors, master/slave processors, etc.), distributed processing across multiple components/systems, system on chip (SOC) devices, or the like.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The ring electrodes 34 communicate position signals to ECU 42 through a conventional interface (not shown). In order to avoid introducing undesirable shift or drift into the determined catheter position and orientation based upon readings obtained by the electric-field based positioning system 36, it can be important to know when the catheter electrodes 34 are inside the introducer. In particular, if the catheter electrodes 34 are located inside the introducer, the data coming off of those shielded electrodes may be degraded/compromised.

FIG. 2 depicts a steerable introducer 56 having a sensor 58 (e.g., a proximity sensor) affixed to a cap 60 of a hemostasis valve 62. Although the proximity sensor 58 is depicted as an external component, it could be internal to the handle 64. Also visible in FIG. 2 is a Tuohy-Borst side arm assembly 66, including a Tuohy-Borst adapter 68 and a stopcock 70. A steering actuator 72 is shown at the distal end of the handle 64, and a strain relief 74 (or retaining nut) is shown just distal to the steering actuator 72. An introducer shaft 76 extends rightward in FIG. 2 from the strain relief 74 to an atraumatic tip 78 at the distal end of the shaft. An electrode 80 is also depicted in FIG. 2 near the atraumatic tip 78. A connector 82 is available to electrically connect the sensor 58 to, for example, the ECU 42 (FIG. 1). Finally, the steerable introducer 56 depicted in FIG. 2 may include on-board information storage 84 (e.g., an EEPROM or other memory device) mounted inside the handle housing. The introducer depicted in FIG. 2 is similar to the AGILIS ES steerable introducer manufactured by St. Jude Medical, Inc., of St. Paul, Minn., and is depicted as a representative example of an introducer or other enveloping device in which the principles described herein may be implemented.

FIG. 3 depicts a fixed-curve introducer 86. The fixed-curve introducer has a hemostasis valve 62' at its proximal end. The hemostasis valve includes a cap 60' that includes an annular groove 88 that is configured to accept the gripping arms 90 of a clip-on sensor 92 such as the one depicted in, for example, FIG. 4. The clip-on sensor depicted in FIG. 4 includes a sensor head 94 and a mounting clip 96 comprising the gripping arms 90 shown riding in the annular groove 88 in the hemostasis valve cap 60' of FIG. 3. An electrical connector is depicted in FIG. 3 for electrically connecting the sensor 92 to a navigation system 10 such as the one depicted in FIG. 1. The fixed-curve introducer, as shown in FIG. 3, also includes a Tuohy-Borst side arm assembly 66, including a Tuohy-Borst adapter 68 and a stopcock 70. The fixed-curve introducer depicted in FIG. 3 is similar to a SWARTZ BRAIDED introducer sold by St. Jude Medical, Inc., and is depicted as another representative example of an introducer or other enveloping device in which the principles described herein may be implemented. An atraumatic tip 78' is depicted at the distal end of the introducer shaft 76'. The clip-on sensor 92 is a separate, re-sterilizable device that could be attached to the proximal end of the introducer 86.

FIG. 5 depicts a catheter 14' having a plurality of electrodes 34 for a variety of diagnostic and therapeutic purposes including, for example, electrophysiological studies, catheter identification and location, pacing, and cardiac mapping and ablation. Although the catheter 14', for purposes of this invention, could be a therapy or diagnostic catheter, the catheter depicted in FIG. 5 is most similar to the SAFIRE ablation catheter manufactured by St. Jude Medical, Inc., and is depicted as a representative example of a catheter or other advanceable intrabody device in which the principles described herein may be implemented.

In FIG. 5, a marker band 98 is shown near the proximal end of the catheter shaft 28'. The marker band could extend around the entire circumference of the catheter shaft, or it could be one or more arcuate pieces rather than a complete ring. The marker band 98 could also be an embedded spot or puck or other recessed, detectable component (e.g., lines or tick marks like the transverse markings on a tape measure). The marker band 98 could be molded into or applied to the surface of the catheter shaft 28'; and, the marker band could be added to the catheter shaft during assembly of the catheter, or it could be added at a later time, including just prior to a procedure in an electrophysiology (EP) lab. The application of marker bands on catheter shafts, "on the fly" in an EP lab is discussed further below in connection with FIGS. 21 and 22.

Preferably, the marker band or bands 98 on the catheter shaft are flush or nearly flush with the outer surface of the catheter shaft 28' so that they may fit through the seal in the hemostasis valve (62 or 62' or 62") of the steerable or fixed-curve introducer 56, 86, respectively. However, an enlarged marker band (not shown) that does not fit through the hemostasis valve could be used if the physician or clinician only wanted to know when the most proximal ring electrode exits the distal end of the introducer. At that point, the enlarged marker band could actually come into physical contact with the proximal side of the hemostasis valve and, alternatively, be simultaneously sensed by the sensor 58 and reported to the navigation system 10. Similar to what was described in connection with the introducer shown in FIG. 2, the catheter depicted in FIG. 5 may also include on-board storage 84' such as an EEPROM, shown in FIG. 5 as being mounted within the catheter handle housing. The EEPROM could store, for example, information about the location of the marker band, including the distance from the marker band to the tip electrode along the catheter shaft, and/or the distance from the marker band to the most-proximal ring electrode, and/or the distance from the marker band to each of a plurality of ring electrodes on the catheter shaft. When the catheter is connected via the electrical connector 26 to the navigation system depicted in FIG. 1, the navigation system could thereby learn about the marker band and its placement along the catheter shaft. Finally, a light 100 (e.g., an LED) may be present on the catheter handle 24' as explained further below.

FIG. 6 depicts a catheter assembly 102, comprising the catheter 14' shown in FIG. 5 inserted into the steerable introducer 56 shown in FIG. 2. When the catheter shaft 28' is inserted down the throat of the introducer as shown in FIG. 6, the distal end of the catheter shaft protrudes from the sheath distal end. In this particular embodiment, when the most proximal catheter electrode exits the distal end of the sheath, a marker band is detected by the proximity sensor 58, and the indicator light 100 lights up. Alternatively, the indicator light 100 could be red until the marker band 98 is detected by the proximity sensor and then go out or turn green. Other feedback may be used in lieu of or in addition to visual feedback, such as audible, tactile (e.g., vibratory) and/or other perceivable feedback. The fact that the most proximal catheter electrode has exited from the distal end of the introducer shaft 76 may also be reported through the connector 82 to the navigation system 10 depicted in FIG. 1. The navigation system relies upon knowing that the ring electrodes and tip electrode 34 are not within the introducer shaft 76. If one or more of the ring electrodes, for example, are retracted into the introducer shaft 76, the navigation system receives degraded or compromised data and may miscalculate or be completely unable to determine where the catheter is located within, for example, an anatomical model of the patient's heart.

FIG. 7 is an enlarged view of the circled region of FIG. 6, depicting a most-proximal catheter electrode 104 adjacent to the distal end 106 of the introducer shaft 76.

FIGS. 8 and 9 schematically depict the steerable introducer 56 and catheter 14' shown in, for example, FIG. 6. As shown in FIG. 8, the marker band 98 on the catheter 14' is detected by the proximity sensor 58 on the introducer 56 as the most-proximal ring electrode 104 exits from the distal end of the introducer 106. The compatibility of a given introducer with a given catheter is determined by ensuring that the distance from the proximity sensor 58 to the distal end 106 of the introducer 56 is the same as the distance from the marker band 98 to the most-proximal ring electrode 104 of the catheter 14'. These two distances are both represented as 'D' in FIGS. 8 and 9. In FIG. 9, as represented by the arrow 108, the catheter 14' has been moved proximally (i.e., leftward in this figure), thereby retracting the most proximal ring electrode 104 into the introducer shaft 76. At that point, the navigation system would no longer receive accurate information from the most proximal ring electrode 104. At that point, the navigation system could be configured to ignore the data being collected from the most proximal electrode 104, or ignore the data being collected from all of the electrodes 34, depending upon the desired settings for a particular physician.

The embodiments shown in FIGS. 5-9 actively measure or indicate only when the most proximal electrode 104 enters the introducer shaft 76. It may, however, be desirable to know when each of a plurality of electrodes on the catheter enters into or exits from the distal end of the introducer. A couple of configurations capable of supplying that higher resolution information are described next.

Figure 10:
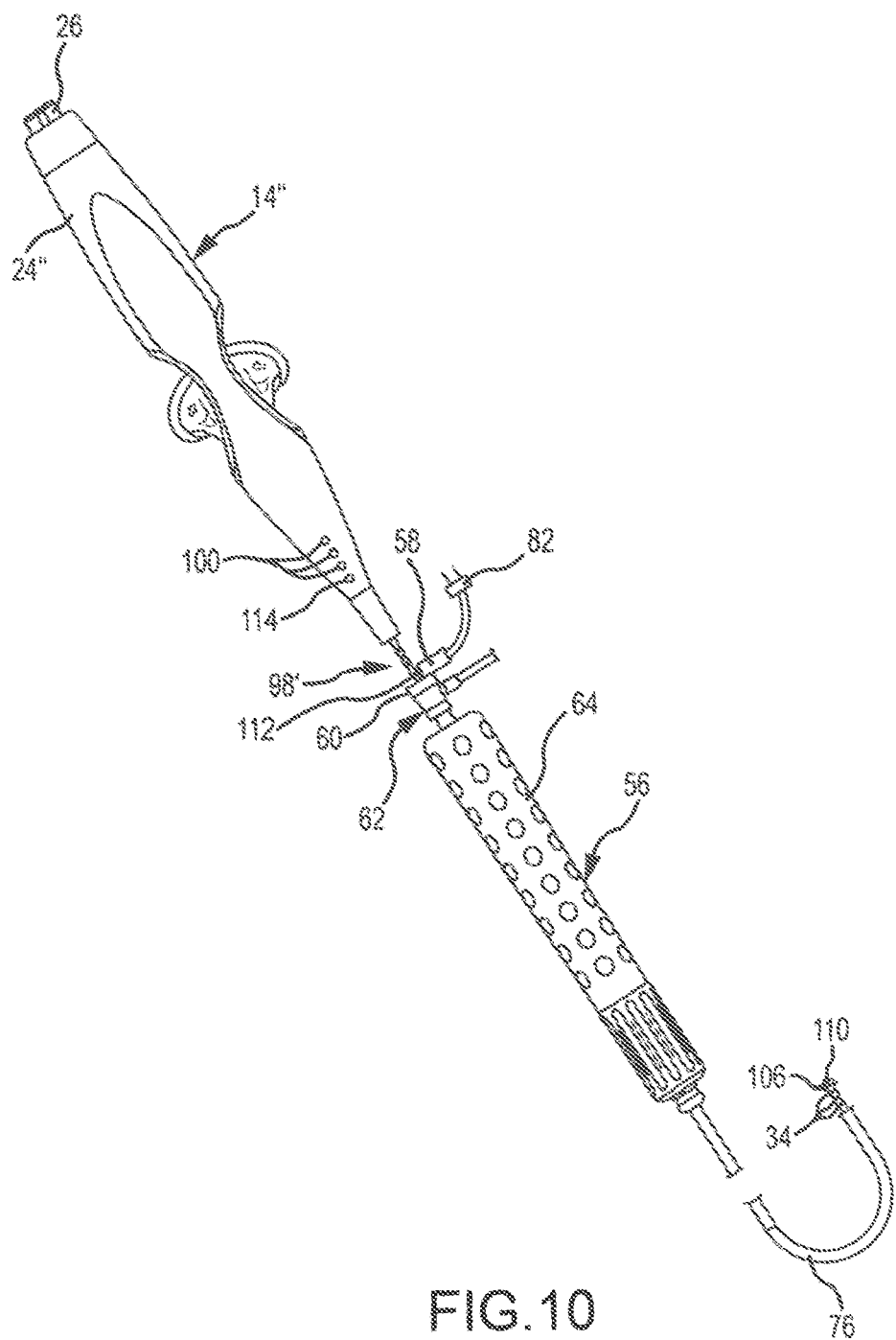
FIG. 10 is similar to FIG. 6, but depicts an assembly where the catheter comprises multiple marker bands on the proximal portion of the catheter shaft and multiple indicator lights on the catheter handle housing.

FIG. 10 is similar to FIG. 6, but depicts a catheter 14" having a plurality of marker bands 98' on the catheter shaft portion closest to the catheter handle 24". In this particular configuration, there is a separate marker band for each ring electrode and a separate marker band for the tip electrode. In the configuration and relative placement of the catheter 14" and introducer 56 shown in FIG. 10, the tip electrode 110 is right at the distal 106 end of the introducer shaft 76. Thus, the marker band 112 for the tip electrode 110 is shown just passing the sensor 58. In FIG. 10, the distal portion of the introducer shaft wall is broken away to reveal the fact that the three ring electrodes 34 are inside the sheath. The marker bands corresponding to these electrodes are, therefore, still proximal to the sensor 58. That is, the marker bands corresponding to the ring electrodes have not yet passed under the sensor that is attached to the proximal side of the cap 60 on the hemostasis valve 62.

FIG. 11 is similar to FIGS. 8 and 9 and schematically depicts a marker band and electrode configuration that is also depicted in FIG. 10. As clearly shown in FIG. 11, there is a separate marker band for each of the three electrodes and a single marker band for the tip electrode. Each marker band is separated from its ring or tip electrode by a distance D, which corresponds to the internal length of the introducer. This configuration is, therefore, able to provide information to the navigation system and thus to the clinician when each of the ring electrodes is retracted into the introducer and thus stops supplying reliable location data or patient information to the navigation system. As shown in FIG. 10, the catheter handle 24" may include a LED 100 for each of the ring electrodes 34 and an LED 114 for the tip electrode 110. As previously discussed, these indicator lights or LEDs may be visual indicators to the physician about how many and which electrodes are currently providing reliable data to the navigation system 10.

Figures 12, 13:
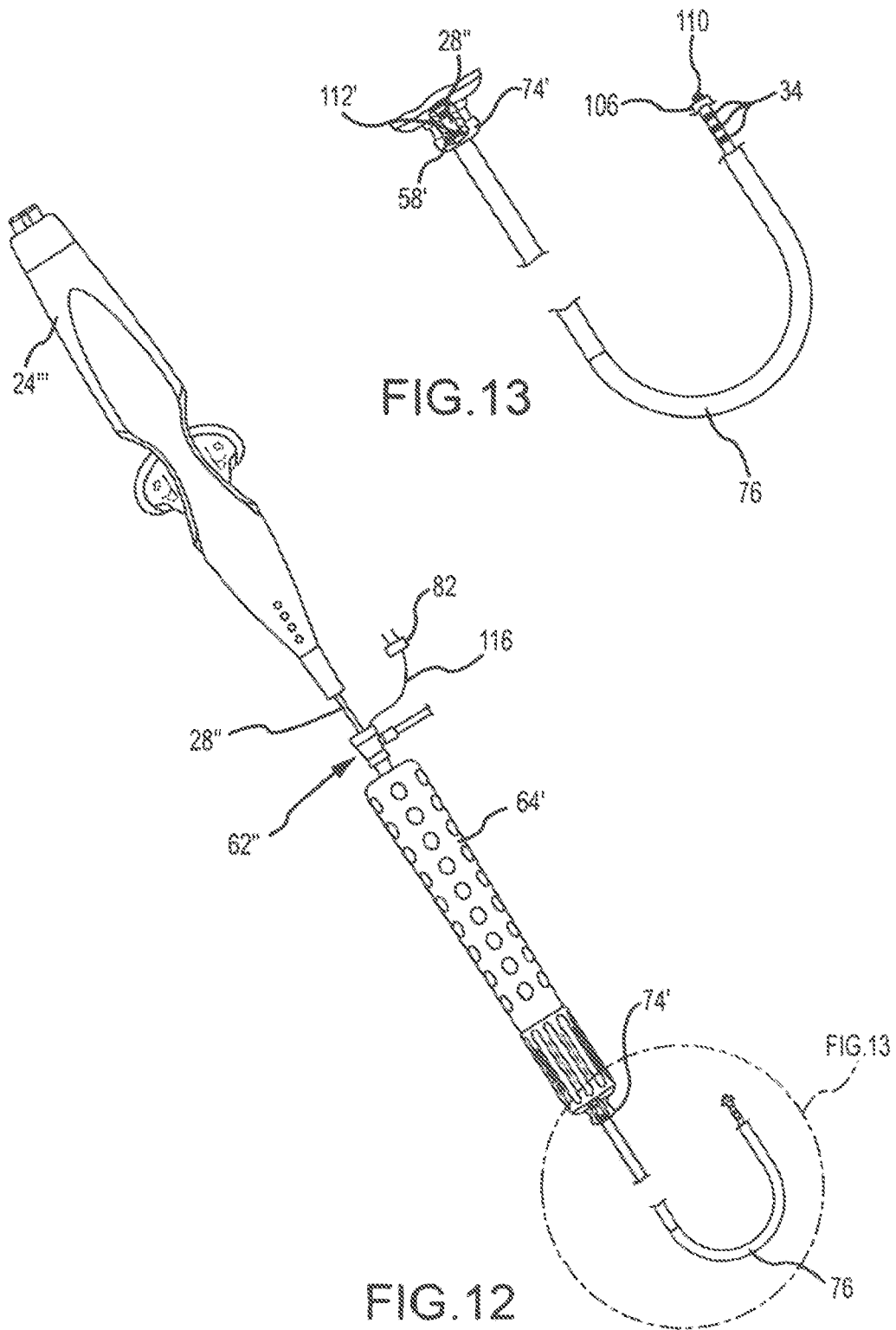
FIG. 12 is similar to FIGS. 6 and 10, but depicts a catheter having a plurality of marker bands at a more distal location on the catheter shaft than what is depicted in FIGS. 6-11, and wherein the sensor is located at the distal end of the introducer handle.
FIG. 13 depicts an enlarged view of the circled portion of FIG. 12.
Figure 14:
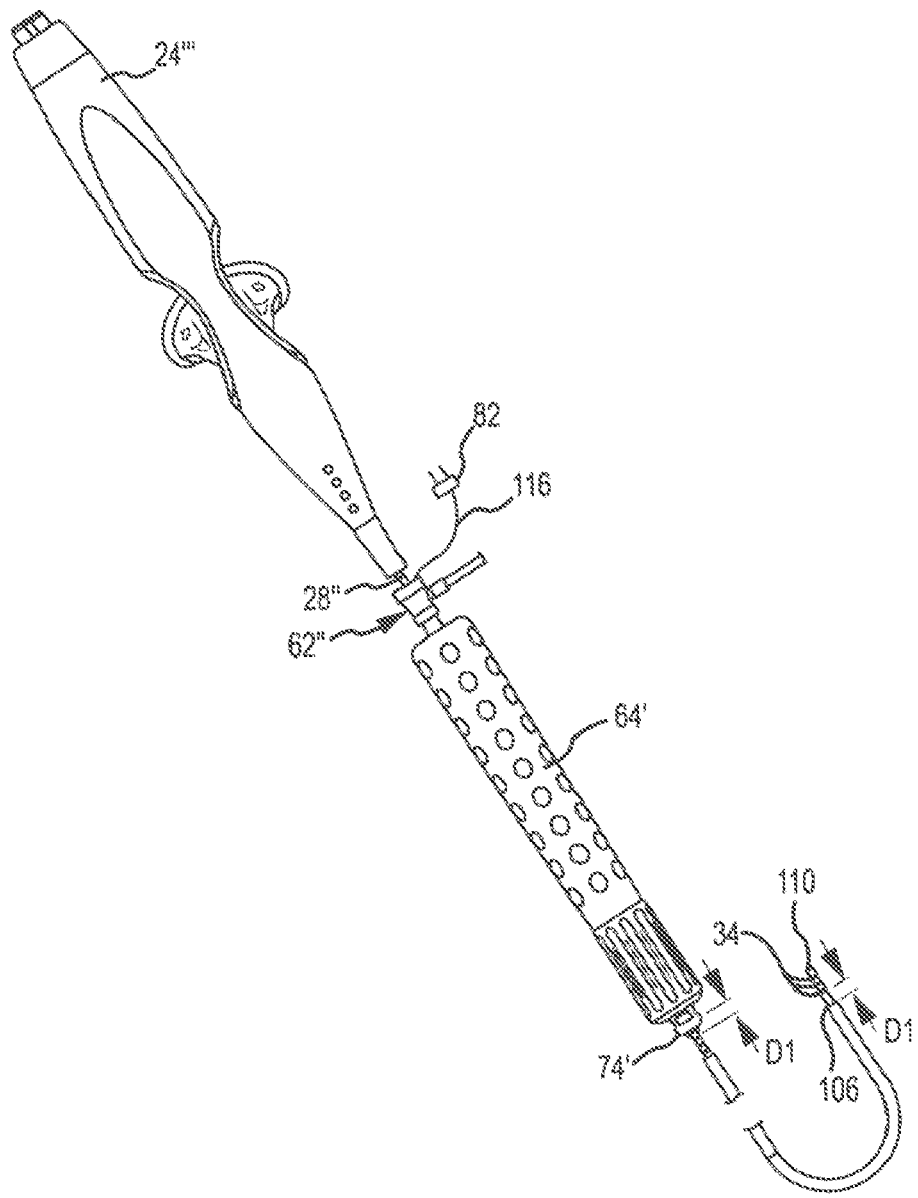
FIG. 14 depicts the catheter and introducer also shown in FIG. 12, but with the catheter inserted more distally in the introducer, such that the ring electrodes at the distal end of the catheter shaft have all exited the distal end of the introducer shaft.

FIGS. 12-14 depict another embodiment. In this particular embodiment, the sensor 58' (see FIG. 13) has been moved from the hemostasis valve 62" to the strain relief 74' at the distal end of the steerable introducer handle 64'. This may be clearly seen in FIG. 13 which is an enlarged view of the circled portion of FIG. 12. As shown in FIG. 13, the sensor 58' (e.g., a proximity sensor) is embedded in a sidewall adjacent to the inner surface of the introducer shaft and positioned to sense the passing of marker bands on the catheter shaft. In FIGS. 12 and 13, a portion of the strain relief member 74' is broken away so that you can see not only the proximity sensor 58', but also the marker bands on the catheter shaft 28". Similarly, a portion of the introducer sidewall is broken away near the distal end 106 of the introducer so that it is possible to see that the ring electrodes 34 at the distal end of the catheter shaft are inside the introducer and the tip electrode 110 is just exiting the distal end 106 of the introducer shaft 76. The marker band 112' corresponding to the tip electrode is, therefore, just passing by the proximity sensor 58' embedded in the strain relief member 74'. In order to transfer signals from the proximity sensor to the navigation system in this embodiment, an electrical lead 116 would extend to the strain relief member 74' (e.g., inside of the steerable introducer handle), FIG. 14 is similar to FIG. 12; however, in FIG. 14 the catheter has been inserted deeper into the introducer. At this point, the tip electrode 110 and all three ring electrodes 34 at the distal end of the catheter are extended from the distal end of the introducer. The distance D1 is the distance from the most proximal ring electrode to the distal end of the introducer, and is also the distance from the most proximal marker band to the proximity sensor mounted in the strain relief member. Again, the catheter handle may include a series of lights to provide visual feedback, and/or audible, tactile or other feedback to a physician as to a number of electrodes providing reliable location data to a navigation system at any point in time.

As described herein, a catheter shaft may be equipped or otherwise configured to accommodate the detection of its own electrodes traversing a distal opening on a partnering introducer. In one embodiment, a catheter, such as catheter 14', includes a catheter shaft 28'. The catheter shaft 28' may include one or more electrodes, such as ring electrodes 34, at its distal portion. The catheter shaft 28' may further include at least one detectable marker 98 positioned proximal to the electrode(s) 34 at the distal portion of the shaft 28'. The detectable marker 98 may be positioned a predetermined distance, such as distance D of FIGS. 8 and 9, from a most proximal electrode 104 of the electrode(s) 34. In one embodiment, the predetermined distance D may correspond to a distance from a distal opening at the tip 78 of an interoperable introducer, such as introducers 56/86, to a marker detector (e.g., sensors 58, 58', sensor head 94, etc.) positioned along the introducer proximal to its distal opening. In another embodiment, one or more additional detectable markers 98' may each be positioned proximal to a plurality of the electrodes 34 at the distal portion of the shaft 28', where each of the detectable markers 98' is positioned a predetermined distance D from a respective one of the plurality the electrodes 34.

Since it may be critical to be able to discern which electrodes and how many electrodes are extending past the distal end of the introducer at any particular time, it can be advantageous to sense the location of the electrodes from the distal end of the introducer. In the configuration depicted in FIG. 6, the sensed marker bands are displaced a substantial distance from the electrodes. In the configurations depicted in, for example, FIGS. 12-14, the sensed marker bands have been moved closer to the distal end of the introducer. In the embodiments depicted in FIGS. 15-18, the electrodes are being detected right at the distal end of the introducer.

Figure 15:
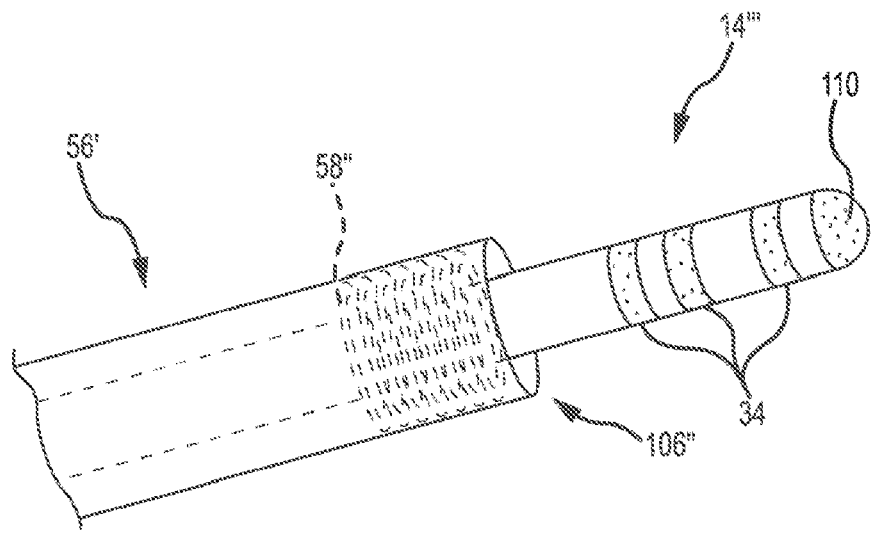
FIG. 15 is a fragmentary, isometric view of a distal end of an introducer with the distal end of a catheter projecting from it, and wherein sensors are depicted in phantom embedded in the sidewall at a distal end of the introducer.

In FIG. 15, the distal portion of the catheter 14''' is shown extending slightly past the distal end 106" of the introducer 56', Proximity sensors 58" at the distal end of the introducer 56' are shown in dashed lines. In this configuration, the sensors may be, for example, inductive-type sensor coils. In order to provide corresponding data to the navigation system 10, a lead wire (not shown) would preferably run in the sidewall of the introducer 56' from the sensors 58" to the connector 82 at the proximal end of the introducer. Providing lead wires in the sidewall of an introducer can create some manufacturing challenges and may undesirably reduce the inside diameter of the introducer that is available for catheters.

Figure 16:
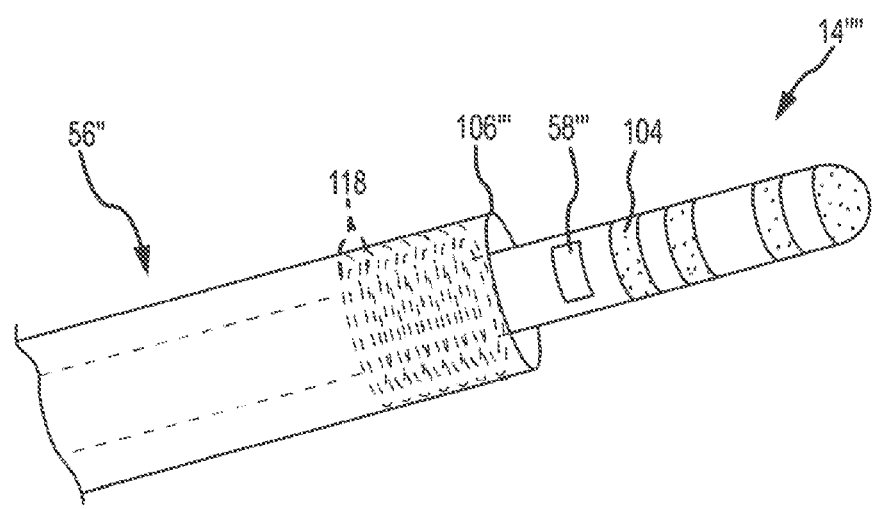
FIG. 16 is most similar to FIG. 15, but depicts a sensor embedded in the catheter shaft just proximal to the most proximal ring electrode.

In the embodiments depicted in FIG. 16, the proximity sensor 58''' has been moved to a location on the shaft of the catheter 14'''' just proximal of the most-proximal ring electrode 104. This proximity sensor 58''' could be configured to detect when it passes the coils or rings 118 mounted in the distal end 106''' of the introducer 56".

Figure 17:
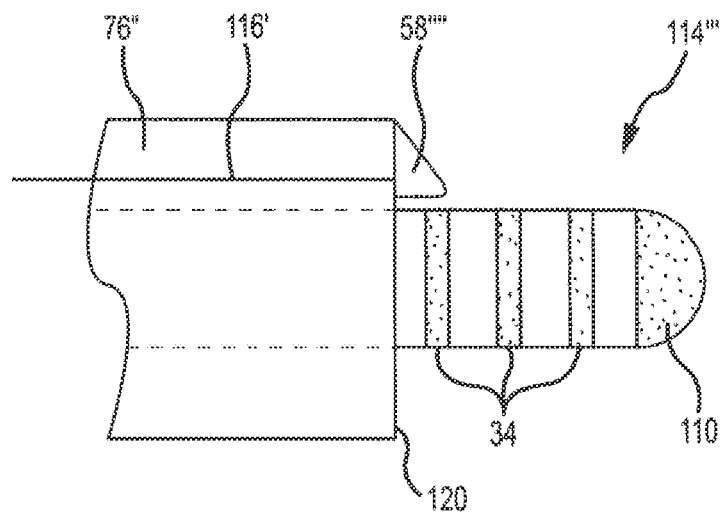
FIG. 17 is a fragmentary view showing the distal end of an introducer having a sensor/detector projecting distally from a distal surface of the introducer and placed to sense or detect catheter electrodes passing by it as those electrodes exit from, or enter into, the introducer.

In the embodiment of FIG. 17, a sensor/detector 58'''' projects from the distal surface 120 of the introducer shaft 76". The sensor/detector 58'''' is configured to detect passage of the ring electrodes 34 and tip electrode 110 from the distal end of the introducer. This data would be reported back to the navigation system 10 through the electrical lead 116'.

Figure 18:
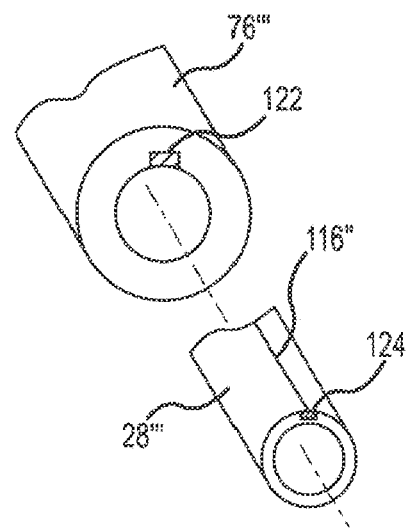
FIG. 18 is a fragmentary, isometric view that schematically depicts an introducer shaft having a first element embedded in its inner sidewall and a catheter shaft having a complementary element embedded in its outer sidewall, such that the first element and the second element pass near each other as the catheter moves relative to the introducer.

FIG. 18 is a fragmentary, schematic view of a distal portion of an introducer shaft 76''' and a distal portion of a catheter shaft 28'''. A first element 122 is depicted embedded in the inner wall of the introducer shaft 76''' adjacent the distal end surface of the introducer shaft. A second element 124 is shown embedded in the outer surface of the catheter shaft 28'''. As these two elements pass each other, information could be communicated back to the navigation system 10 concerning the location of catheter shaft electrodes vis-à-vis the end of the introducer. One of these elements 122, 124 would be a sensed element and the other one would be a sensor. Thus, an electrical lead 116" would run from at least one of these elements back to the navigation system 10. In FIG. 18, the lead 116" is shown connected to the second element 124.

Figure 19:
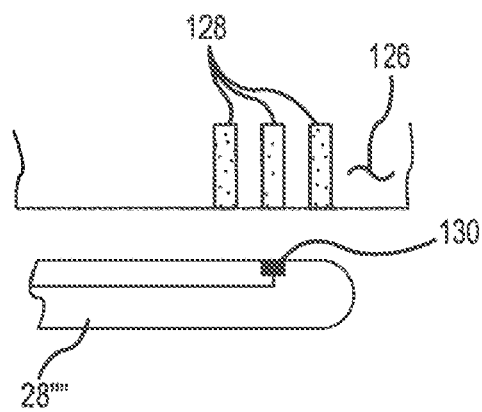
FIG. 19 schematically depicts the inner wall of an introducer having marker bands or stripes on it, and a catheter passing by the marker bands or stripes, the catheter having a sensor embedded in its outer sidewall.

FIG. 19 schematically depicts a section of the inner wall of an introducer shaft above a fragmentary section of a catheter shaft 28''''. The inner wall 126 of the introducer is shown with a plurality of marker bands or stripes 128 on it, and the catheter shaft is depicted with a single sensor 130 arranged to pass closely adjacent to the bands 128 on the inner wall 126 of the introducer. The bands or stripes 128 on the inner wall of the introducer could be located anywhere on the length of the introducer. In one configuration, each band has a different color and the sensor 130 is able to detect color. The sensor is thus able to report back to the navigation system 10 which band it is closest to, which would allow the navigation system to determine which electrode or electrodes must be extending from the distal end of the introducer, if any. The sensor may also be able to detect a direction of travel of the catheter shaft relative to the introducer after the sensor passes at least two bands.

Figure 20:
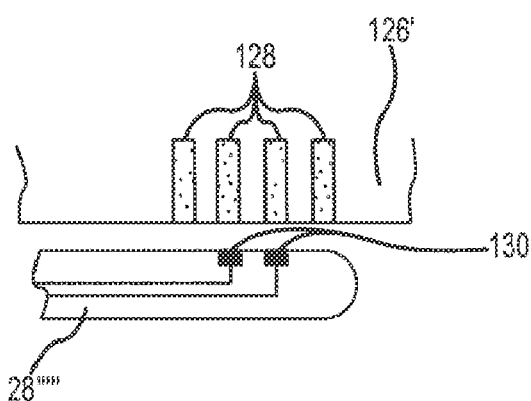
FIG. 20 is similar to FIG. 19, but depicts a catheter having multiple sensors embedded in its sidewall to quickly detect a direction of motion of the catheter relative to the introducer.

FIG. 20 is similar to FIG. 19, but depicts a catheter shaft 28' having a plurality of sensors 130 mounted and configured to read the plurality of marker bands 128 on the inner wall 126' of an introducer. This two-sensor configuration would be able to provide both location and directionality information to a navigation system.

Figure 21:
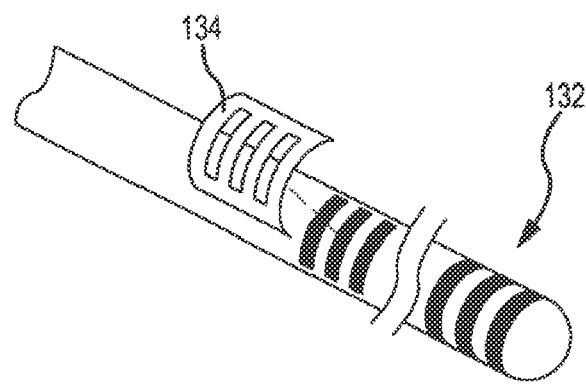
FIG. 21 is a fragmentary, isometric view of the distal end of an off-the-shelf catheter and a stencil hovering above the surface of the catheter, the stencil being used to apply marker bands to the outer surface of the catheter.

FIG. 21 is an isometric, fragmentary view of the distal portion of an off-the-shelf catheter 132. In this figure, a stencil 134 is shown exploded away from the outer surface of the catheter 132. The stencil could be used to apply marker band material to create marker bands on the outer surface of an off-the-shelf catheter while in, for example, the EP lab. This embodiment contemplates having a plurality of stencils, possibly one stencil for each of a variety of different types or brands of catheters. Using an appropriate stencil, a physician or technician could 'paint on' or 'apply' marker hands to the catheter of his or her choice, thereby also permitting the navigation system to determine when the catheter electrodes are outside of the sheath and available for reporting accurate location information.

Figure 22:
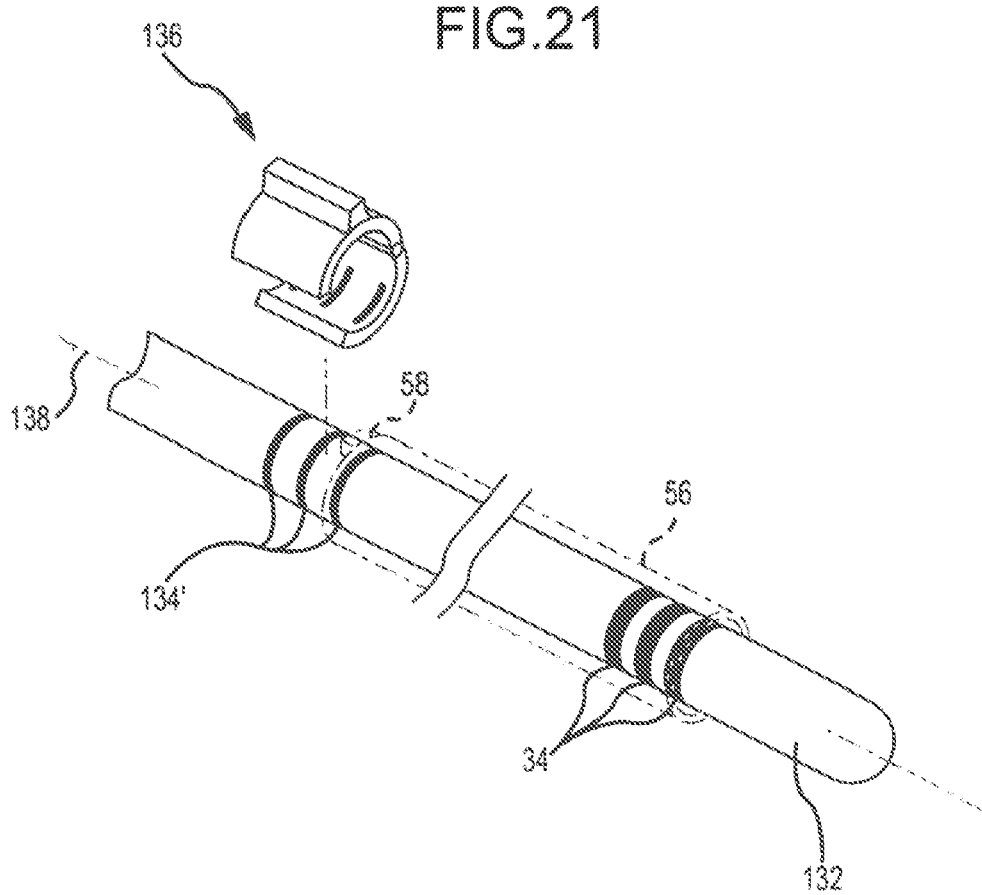
FIG. 22 depicts a distal end of an off-the-shelf catheter passing through an introducer (shown in phantom), and depicts an ancillary device hovering above the catheter shall, the ancillary device being adapted to apply or 'paint' marker bands onto the catheter.

FIG. 22 is a fragmentary, isometric view of an off-the-shelf catheter 132 mounted in an introducer 56 (shown schematically in phantom in this figure). As clearly depicted in FIG. 22, the catheter 132 has three ring electrodes 34 at its distal end. The most distal ring electrode is shown in FIG. 22 about to exit from the distal end of the introducer 56. Three marker bands 134', corresponding to the three ring electrodes 34, are also depicted in FIG. 22. The most distal marker band is shown about to pass under a proximity sensor 58 on the introducer since the most distal of ring electrodes 34 is about to exit the introducer 56. Hovering above the marker bands 134' is an ancillary device 136 that was used to put the marker bands on the catheter shaft. In particular, this reusable, ancillary device 136 may temporarily and removably clamp on or around a catheter shaft to apply marker bands to an off-the-shelf catheter. The ancillary device 136 could be clamped around the catheter shaft and then rotated about the catheter shaft's longitudinal axis 138 in order to draw arcuate or circumferential marker bands on the shaft. Once the bands have been placed on the shaft, the ancillary device would be removed before inserting the catheter into the introducer.

A system 10 and method for navigating a medical device within a body 12 in accordance with the present teachings enables consistent correction of errors in position measurements due to shift or drift in patient impedance levels. Further, the system 10 and method do not require the use of an additional reference catheter and the resulting increases in procedure time and risks.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counterclockwise" may be used herein with respect to the illustrated embodiments. However, medical instruments may be used in many orientations and positions, and these terms are not intended to be limiting and absolute. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system comprising:
   an electric-field-based positioning system;
   a catheter including a marker band and an electrode located at a distance from the marker band;
   an introducer including a proximity sensor adapted to sense the marker band, wherein the distance between the proximity sensor and a distal end of the introducer corresponds to the distance between the marker band and the electrode; and
   an electronic control unit (ECU) electrically coupled to said electric-field-based positioning system and operable to do the following:
      drive currents through a plurality of patch electrodes on a surface of the body and measure a resulting voltage from the catheter electrode;
      monitor a first signal originating from the proximity sensor to determine when the marker band passes the proximity sensor;
      analyze said first signal to determine whether the catheter electrode is within the introducer; and
      disregard said measured resulting voltage if the catheter electrode is within the introducer.

2. The system of claim 1, wherein the ECU is further operable to
   generate a map of a portion of the human body using the measured resulting voltage if the catheter electrode is outside the introducer.

3. The system of claim 2, wherein the first memory device is an EEPROM.

4. The system of claim 1, wherein the catheter further comprises a first memory device adapted to store dimension information about the catheter including an overall length of the catheter and a location of the at least one marker band and wherein the ECU reads the dimension information in analyzing the first signal to determine whether the catheter electrode is within the introducer.

5. The system of claim 4 further comprising a display, and where the ECU is further operable to indicate, using a signal from the ECU, on the display when the ECU disregards the measured resulting voltage, where the indication comprises one or more of a value, an illuminated light, text, and a sound.

6. The system of claim 1, wherein the ECU is further operable to do the following:
   monitor a second signal originating from the proximity sensor to determine when a second marker band passes the proximity sensor, where the second marker band corresponds to a second catheter electrode;
   display a value representing the number of signals originating from the proximity sensor.

7. The system of claim 6, wherein a position of each marker band is proximal to the proximity sensor and corresponds to a respective catheter electrode proximal a distal end of the introducer, and wherein the ECU is further operable to determine, based on the respective marker bands passing the proximity sensor, when each respective catheter electrode enters or exits the introducer.

8. The system of claim 1, where the ECU is further operable to indicate to a user, using a signal from the ECU, when the ECU disregards the measured resulting voltage.

9. The system of claim 1, where the ECU is further operable to indicate to a user, using a signal from the ECU, when the catheter electrode exits or enters the introducer.

10. A system for detecting when a sensed element on a first medical device enters into or exits from an introducer, the system comprising:
    a first storage operable to store (i) first location data relating to a location of the sensed element on the first medical device, (ii) second location data relating to a location of a sensor on the introducer, and (iii) a distance from the sensed element to an electrode on the first medical device;

a second storage operable to store current position and orientation data relating to the first medical device;

a device operable to determine a position of the sensor; and a processor in communication with the first storage, the second storage, and the first medical device, wherein the processor is operable to do the following:
  determine a position of the electrode relative to the introducer based on the location of the sensed element and the distance between the sensed element and the electrode;
  determine whether to disregard or use the current position and orientation data for the first medical device based on whether the electrode is within the introducer; and
  output a signal indicative of whether the current position and orientation data for the first medical device is being disregarded or used.

11. The system of claim 10, wherein the first location data and the second location data are indicative of the first medical device entering into or exiting from the introducer.

12. The system of claim 10, wherein the first storage and the second storage are each an EEPROM.

13. The system of claim 10, wherein the processor is further operable to generate a map of a portion of the human body using the current position and orientation data for the first medical device only if processor determines that the sensor is outside the introducer.

14. A method of detecting a relative position of a catheter and an introducer while the catheter and the introducer are in a human body, the catheter comprising a marker band and a catheter electrode located at a distance from the marker band, and the introducer comprising a proximity sensor adapted to sense the marker band, the method comprising:
  driving currents, by an electronic control unit (ECU) electrically coupled to an electric-field-based positioning system, through a plurality of patch electrodes on a surface of the body and measure a resulting voltage from the catheter electrode;
  monitoring, by the ECU, a first signal originating from the proximity sensor to determine when the marker band passes the proximity sensor;
  analyzing, by the ECU, the first signal to determine whether the catheter electrode is within the introducer based on the first signal from the proximity sensor; and
  generating, by the ECU, a map of a portion of the human body using the measured resulting voltage if the catheter electrode is outside the introducer.

15. The method of claim 14, further comprising
  monitoring a second signal originating from the proximity sensor to determine when another of the at least one marker band passes the proximity sensor, where the another of the at least one marker band corresponds to a second catheter electrode; and
  displaying a value representing the number of signals originating from the proximity sensor.

16. The method of claim 15, wherein a position of each marker band of the at least one marker band proximal the proximity sensor corresponds to the respective catheter electrode proximal a distal end of the introducer and the ECU is further operable to determine when each respective catheter electrode enters or exits the introducer based on the respective marker bands passing the proximity sensor.

* * * * *